United States Patent [19]
Fukui et al.

[11] Patent Number: 4,985,636
[45] Date of Patent: Jan. 15, 1991

[54] MEDIUM DETECTING SYSTEM WITH AUTOMATIC COMPENSATION FOR SENSOR VARIATIONS

[75] Inventors: Tsutomu Fukui; Hideto Koike; Kemmi Ayukai, all of Tokyo, Japan

[73] Assignee: Oki Electric Industry Co., Ltd., Tokyo, Japan

[21] Appl. No.: 399,931

[22] Filed: Aug. 29, 1989

[30] Foreign Application Priority Data

Sep. 2, 1988 [JP] Japan .................. 63-220234
Aug. 24, 1989 [JP] Japan .................. 1-218075
Aug. 24, 1989 [JP] Japan .................. 1-98745

[51] Int. Cl.$^5$ .................. G01N 21/86; G06K 9/00
[52] U.S. Cl. .................. 250/559; 250/556; 356/71
[58] Field of Search .............. 250/559, 560, 561, 562, 250/563, 208.2, 223 R, 556; 356/429, 384–387, 71; 382/7

[56] References Cited

U.S. PATENT DOCUMENTS

4,559,452 12/1985 Igaki et al. .................. 250/561

Primary Examiner—Edward P. Westin
Attorney, Agent, or Firm—Spencer & Frank

[57] ABSTRACT

In a medium detecting system having a plurality of optical sensors, each including a light-emitting element and a light-receiving element whose current varies with the amount of light received, and a load resistance unit provided in common for the sensors, the resistance of the load resistance circuit can be varied in accordance with load resistance selecting data supplied thereto. A sensor selector is responsive to sensor selecting data for selecting one of the sensors and connecting the light-receiving element of the selected sensor to the load resistance unit. A rewritable memory stores the sensor selecting data and data used for selecting the load resistance.

13 Claims, 9 Drawing Sheets

LOAD RESISTANCE UNIT

| SENSOR SELECTING DATA 13a | | LOAD RESISTANCE SETTING DATA 13b | | REFERENCE SETTING DATA 13c | | LATCH ELEMENT SELECTING DATA 13d | |
|---|---|---|---|---|---|---|---|
| ADDRESS | CONTENTS | ADDRESS | CONTENTS | ADDRESS | CONTENTS | ADDRESS | CONTENTS |
| 11 | SEL(1) | 21 | SRL(1) | 31 | SVr(1) | 41 | SLA(1) |
| 12 | SEL(2) | 22 | SRL(2) | 32 | SVr(2) | 42 | SLA(2) |
| 13 | SEL(3) | 23 | SRL(3) | 33 | SVr(3) | 43 | SLA(3) |
| 1n | SEL(n) | 2n | SRL(n) | 3n | SVr(n) | 4n | SLA(n) |

MEDIUM DETECTING SYSTEM WITH AUTOMATIC COMPENSATION FOR SENSOR VARIATIONS

BACKGROUND OF THE INVENTION

The present invention relates to a medium detecting system used in an apparatus for handling media such as paper media, or the like.

A prior-art medium detecting system has a plurality of optical sensors, each formed of a light-emitting element and a light-receiving element, disposed at various locations in the medium handling apparatus to detect the medium. A variable load resistor is provided in common for the light-receiving elements of a plurality of the sensors. The variable load resistor permits adjustment of its resistance so as to cope with variations in the characteristics of the light-emitting elements and the light-receiving elements, and variations in the percentage of light which is transmitted from the light-emitting elements to the light-receiving elements, due for example to the amount of dust on the light-receiving elements.

This prior-art medium detecting system has the shortcoming that the resistance of the load resistor cannot be adjusted when the medium is not present.

Another problem of the prior art medium detecting system is that the variable resistor has to be manually adjusted.

A further problem of the prior art medium detecting system is that it is not possible to optimize the resistance of the load resistor for each sensor, to cope with variations in the characteristics of the light-emitting elements and the light-receiving elements, variations in the alignment between the light-emitting elements and the light-receiving elements, and variations in the percentage of light which is transmitted from a light-emitting element to its light-receiving element, due for example to the amount of dust on the light-receiving element.

SUMMARY OF THE INVENTION

An object of the invention is to eliminate the above problems.

Another object of the invention is to provide a medium detecting system in which the resistance of a load resistance unit can be adjusted when the medium is not present.

Another object of the invention is to eliminate the necessity of manual adjustment of the load resistance.

A further object of the invention is to enable adjustment of the load resistance for each sensor, to cope with variations in the characteristics of the light-emitting elements and the light-receiving elements, variations in the alignment between the light-emitting elements and the light-receiving elements, and variations in the percentage of light which is transmitted from a light-emitting element to its light-receiving element, due for example to the amount of dust on the light-receiving element.

A medium detecting system according to the invention comprises:

a plurality of optical sensors, each comprising a light-emitting element and a light-receiving element disposed to confront each other so that a medium interposed between the light-emitting element and the light-receiving element interrupts the light transmitted from the light-emitting element to the light-receiving element, the electric current flowing through the light-receiving element varying with the amount of light received by it;

a load resistance unit provided in common for a plurality of the sensors and capable of varying the load resistance responsive to load resistance selecting data;

a sensor selector responsive to sensor selecting data for selecting one of the sensors and connecting the light-receiving element of the selected sensor to the load resistance unit; and a rewritable memory for storing the sensor selecting data and load resistance setting data for the respective sensors, said load resistance setting data being supplied as said load resistance selecting data to the load resistance unit.

DETAILED DESCRIPTION OF THE PREFERRED EMBODIMENTS

Figure 1:
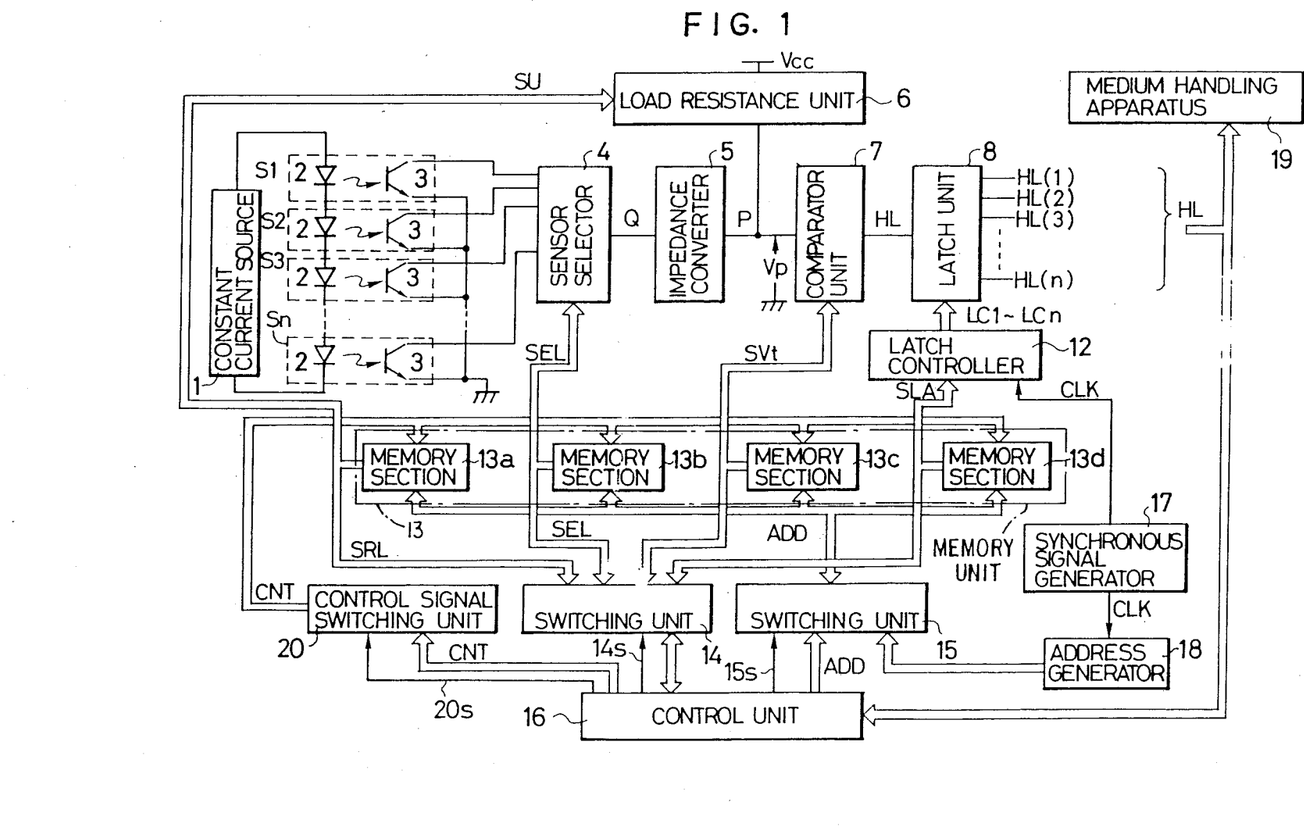
FIG. 1 is a block diagram showing an embodiment of the medium detecting system according to the invention.

An embodiment of the medium detecting system according to the invention is shown in FIG. 1. The term "medium" as used herein encompasses bank notes present in a bank note handling apparatus, and tickets present in a ticket processing machine.

The medium detecting system can operate in a load resistance adjusting mode and a medium detecting mode.

In the load resistance adjusting mode, the resistance of a load resitance unit 6 is optimized by adjustment for each of the sensors Sl and Sn, and the optimized resistance is stored in a memory 13b as load resistance setting data.

In the medium detecting mode, a judgment as to whether or not the medium is present at each of sensors Sl or Sn is performed on the basis of the output of the sensor. The result of the judgment is used by a medium handling apparatus 19.

Elements of the system will now be described in turn.

Sensors Sl to Sn each comprise a light-emitting element, such as a light-emitting diode 2, and a light-receiving element, such as a photo-transistor 3, and are disposed at locations, such as medium transport paths and temporary medium retainers, where the presence of the medium is to be detected. The light-emitting diode 2 and the photo-transistor 3 forming each sensor are disposed so that when the medium to be detected is present on the medium transport path or the temporary retainer, the light path from the light-emitting diode 2 to the photo-transistor 3 is interrupted. Such an interruption reduces the light received by the photo-transistor 3, with the result that the current through the photo-transistor 3 is decreased.

The light-emitting diodes 2 of all the sensors Sl to Sn are connected in series, and a current Id from a constant current source 1 is caused to flow through the light-emitting diodes 2. The emitters of all the photo-transistors 3 are connected to a node at a first potential, such as the ground.

A sensor selector 4 is responsive to sensor selecting data SEL and selects one of the sensors Sl to Sn, and by connecting the collector of the photo-transistor 3 of the selected sensor to a node Q, and by connecting the collectors of the photo-transistors 3 of nonselected sensors to the ground.

Figure 2:
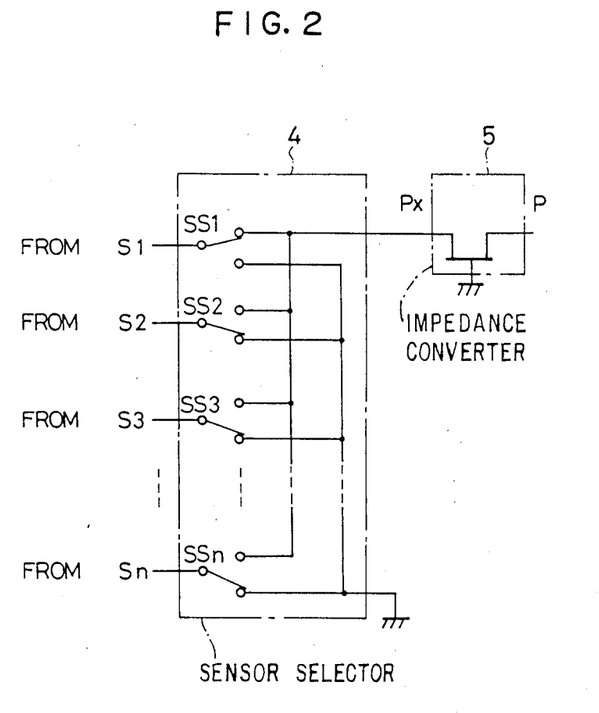
FIG. 2 shows an example of the sensor selector 4 and the impedance converter 5 in FIG. 1.

An example of the sensor selector 4 is shown in FIG. 2. As illustrated, it comprises an array of double-throw analog switches SSl to SSn respectively associated with the sensors Sl to Sn. Each switch has a first electrode connected to the node Q, a second electrode connected to the ground and a third, common electrode connected to the collector of the photo-transistor 3 of the associated sensor. The switches Sl to Sn are controlled responsive to the sensor selecting data SEL from a control unit 16, which will be described later. In the state shown in FIG. 2, the sensor Sl is selected and the other sensors S2 to Sn are not selected.

An impedance converter 5 is provided for accelerating the transition in the photo-current Ic responsive to changes in the amount of light received by the photo-transistor 3. It may, for example, comprise an n-channel MOS FET having a grounded gate electrode, a drain electrode which is connected to the node P, called a sense output node, and a source electrode which is connected the node Q. In other words, the FET is cascode-connected with the photo-transistor 3. As an alternative to the FET, a bipolar transistor may be used. In this case, the base of the transistor should be grounded, the emitter should be connected to the node Q, and the collector should be connected to the node P.

Figure 3:
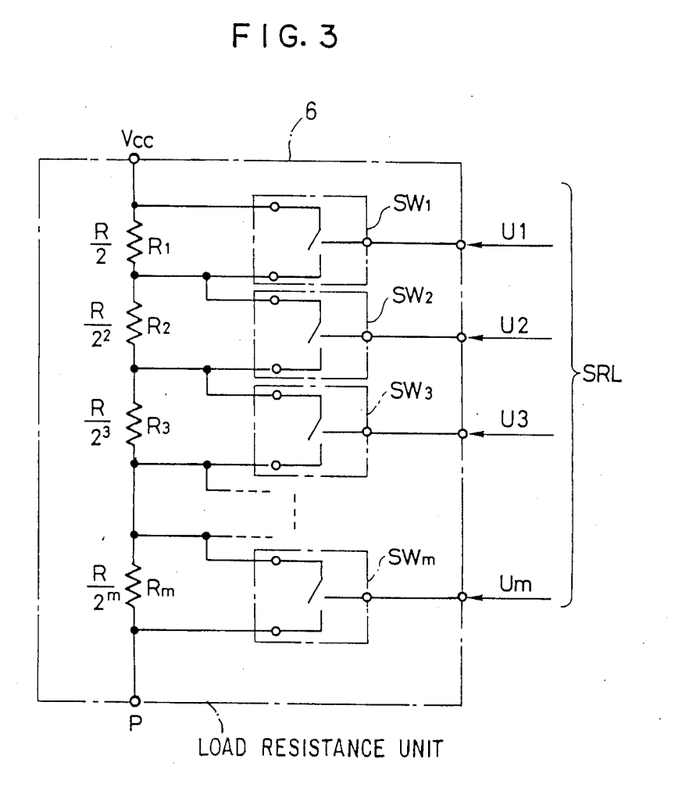
FIG. 3 shows an example of the load resistance unit 6 in FIG. 1.

A variable load resistance unit 6 is provided in common for the photo-transistors 3 of all the sensors Sl to Sn and serves a load resistor for the photo-transistor 3 of the selected sensor. An example of the load resistance unit 6 is shown in FIG. 3. As shown, it comprises a plurality of resistor elements R1 to Rm and analog switches SW1 to SWm for shunting the resistor elements Rl to Rm, respectively. The switches SW1 to SWm are selectively closed or opened, in accordance with binary signals Ul to Um making up the load resistance selecting data SU supplied thereto. (For future reference it is noted that the signals Ul to Um also make up the load resistance setting data SRL, as will be discussed later).

The resistance values of the resistor elements Rl to Rm are set to be $Rw/2, Rw/2^2, Rw/2^3, \ldots Rw/2^m$, respectively, where Rw is a predetermined constant. The binary signals U1, U2, U3, ... Um are variables which set the switches SW1, SW2, SW3, ... SWm, to be closed when they are "0", and to be open when they are "1". The load resistance RL of the load resistance unit 6, i.e., the synthetic resistance between the bias voltage (power supply) Vcc and the sense output node P, is given by:

$$RL = (U1 + U2/2^2 + U3/2^3 + \ldots + Um/2^m)Rw$$

The load resistance RL is 0 when Ul to Um are all "0" and is $(1-\tfrac{1}{2}^m)$ Rw when Ul to Um are all "1". The resolution (minimum step) of the adjustment of the resistance RL is $Rw/2^m$.

Figure 4:
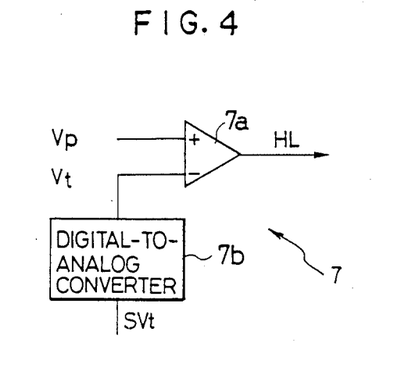
FIG. 4 shows an example of a comparator unit 7 in FIG. 1.

A comparator unit 7 may comprise a voltage comparator element, such as an operational amplifier 7a, and a digital-to-analog converter 7b, as shown in FIG. 4. The digital-to-analog converter 7b receives threshold selecting data SVt and produces a threshold voltage Vt. The operational amplifier 7a compares the sense output voltage Vp (at the sense output node P) with the threshold voltage Vt, and produces an High level output when the former is larger (i.e., the photo-current Ic through the photo-transistor 3 is small), and a Low level output when the former is smaller (i.e., the photo-current Ic through the photo-transistor 3 is large).

Figure 5:
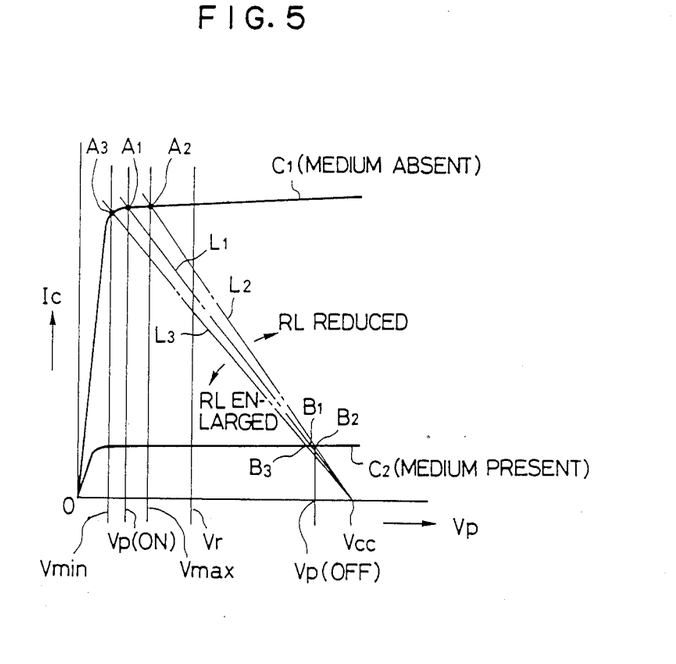
FIG. 5 shows the output characteristics of a sensor and the load resistance unit in FIG. 1.

FIG. 5 shows the output characteristics of a sensor and the load resistance circuit of FIG. 1. If the medium is not present between the light-emitting diode 2 and the photo-transistor 3 (the medium absent state), the amount of light received by the photo-transistor 3 is large and the photo-current Ic is therefore large, so that the voltage-current characteristic of the photo-transistor 3 is as indicated by curve C1. When the medium is present between the light-emitting diode 2 and the photo-transistor 3 (the medium present state), the amount of light received by the photo-transistor 3 is small and the photo-current Ic is therefore small, so that the voltage-current characteristic of the photo-transistor 3 is as indicated by curve C2.

The sense output voltage Vp which appears at the sense output node P and is therefore input to the comparator circuit 7 is at Vp(OFF) when the medium is not present, and is at Vp(ON) when the medium is present. These are the voltages corresponding to the intersections A1 and B1 of the curves C1 and C2 with the line L1 represented by:

$$Ic = (Vcc - Vp)/387ps$$

Figure 6:
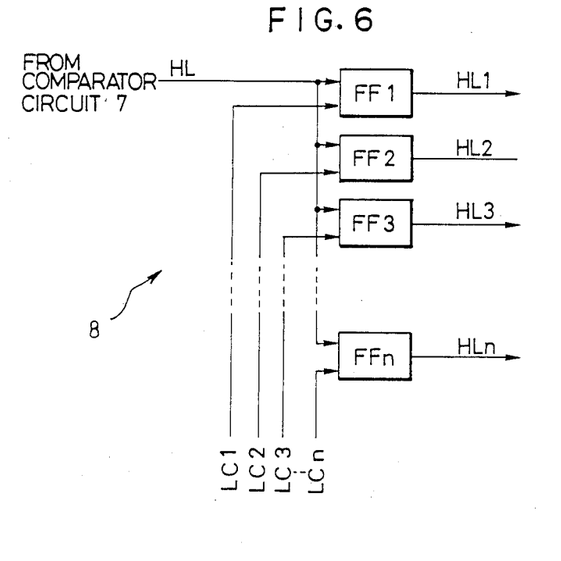
FIG. 6 shows an example of a latch unit 8 in FIG. 1.

A latch unit 8 comprises, as shown in FIG. 6, a plurality of latch elements, e.g., flip-flops FF1 to FFn, corresponding to respective sensors Sl to Sn. Each of the flip-flops FF1 to FFn latches the output HL of the comparator unit 7 when it receives a latch clock signal (that is, the corresponding one of latch clock signals LC1 to LCn). The latch clock signals LC1 to LCn are supplied to the flip-flops FF1 to FFn when the corresponding sensor is selected, or more precisely when the result of the comparison using the output from the corresponding sensor appears at output of the comparator unit 7.

A latch controller 12 controls the operation of the latch unit 8. It receives latch element selecting data SLA indicating which latch element should latch the comparator output HL (this of course is in accordance with the sensor being selected) and produces the latch clock signals LC1 to LCn. The latch clock signals LC1 to LCn are produced when the comparator output HL (obtained as a result of the comparison using the sense output voltage Vp from the corresponding sensor) has been produced and has stabilized, i.e., a predetermined time t after the switching at the sensor selector 4 from one sensor to another.

A clock generator 17 generates synchronous clock signals CLK for synchronizing the supply of the address from an address generator 18, which will be described later, and for producing latch clock signals LC1 to LCn. It is controlled by the control unit 16.

Figure 7:
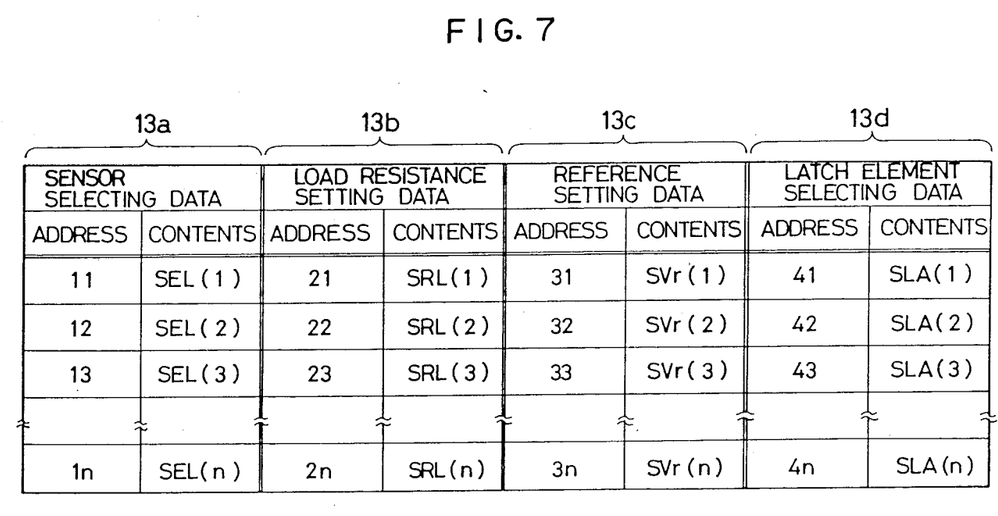
FIG. 7 shows an example of the memory unit 13 in FIG. 1.

The memory unit 13 comprises memory sections 13a to 13d as shown in FIG. 7. The memory sections 13a to 13d store the sensor selecting data SEL (1) to SEL (n), along with load resistance setting data SRL (1) to SRL (n), reference setting data SVr (1) to SVr (n), and latch element selecting data SLA (1) to SLA (n), for the respective sensors S1 to Sn. Although not illustrated, the memory unit 13 also stores upper and lower limit data SVmax and SVmin for the respective sensors S1 to Sn.

The control unit 16 is comprised of a microprocessor with a program memory. In accordance with the program, it controls the sensor selector 4, the load resistance unit 6, the comparator unit 7, and the latch controller 12 during the load resistance adjusting mode. That is, in the load resistance adjusting mode, it generates the addresses for reading the sensor selecting data SEL from the memory unit 13, and performs control for the adjustment of the load resistance.

The address generator 18 generates the addresses used for accessing the memory unit 13 during the medium detecting mode. That is, it generates the addresses for reading the sensor selecting data SEL, the load resistance setting data SRL, and the like.

A data switching unit 14 selectively connects or disconnects the data bus for the control unit 16 with the data bus for the memory unit 13. During the load resistance adjusting mode, it connects the data bus for the memory unit 13 with the data bus for the control unit 16. During the medium detecting mode, it separates the data bus for the memory unit 13 from the data bus for the control unit 16.

An address switching unit 15 selectively connects the address bus for the control unit 16 or the address bus for the address generator 18 with the address bus for the memory unit 13. During the medium detecting mode, it connects the address bus for the address generator 18 with the address bus for the memory unit 13, while separating the address bus for the control unit 16. During the load resistance adjusting mode, it connects the address bus for the control unit 16 with the address bus for the memory unit 13, while separating the address bus for the address generator 18. It then sequentially selects the parts 13a to 13d.

A control signal switching unit 20 switches the control signals from the control unit 16 to the memory unit 13. During the medium detecting mode, it blocks the control signals from the control unit 16 to the memory unit 13, and instead it supplies the memory unit 13 with signals which inhibit rewriting of the data in the memory 13 by the control unit 16. During the load resistance adjusting mode, it allows the control signals from the control unit 16 to be applied to the memory unit 13.

The switching units 14, 15 and 20 are controlled by switch control signals 14s, 15s and 20s, which are either High when the load resistance adjusting mode is designated or Low when the medium detecting mode is designated.

The mode of operation (that is, the medium detecting mode or the load resistance adjusting mode) is selected by instructions from an interface, not shown, in the medium handling apparatus 19.

When a signal for starting the load resistance adjusting mode of operation is supplied from the interface in the medium handling apparatus 19 to the control unit 16, the control unit 16 instructs the data switching unit 14, the address switching unit 15 and the control signal switching unit 20 to operate in the load resistance adjusting mode by means of the switch control signals 14s, 15s and 20s.

Then, the data switching unit 15 connects the data bus for the control unit 16 with the data bus for the memory unit 13, the address switching unit 15 connects the address bus for the control unit 16 with the address bus for the memory unit 13, and the control signal switching unit 20 closes the signal paths from the control unit 16 to the memory unit 13.

In the load resistance adjusting mode, the medium is not present in the transport paths and the temporary retainers, and hence the medium is not present at any of the sensors S1 to Sn.

The adjustment of the load resistance RL for the sensors S1 to Sn is performed in turn, e.g., from the sensor S1 to the sensor Sn in order.

The load resistance RL for each sensor is adjusted so that the sense output voltage Vp at the sense output node P (given at the intersection A1 of the output characteristic line L1 with the curve C1 in FIG. 5) lies between a predetermined upper limit Vmax and a predetermined lower limit Vmin. This is accomplished by successive approximation, e.g., using the binary search method, starting with an arbitrary initial value. The initial value may, for example, be the value set by the "old" load resistance setting data SRL that was determined in the preceding load resistance adjustment and stored in the memory unit 13. A decision is then made as to whether the sense output voltage Vp is larger or smaller than Vmax, Vmin. Depending on the result of the decision, the load resistance RL is increased or decreased. A decision is again made as to whether Vp is larger or smaller than Vmax, Vmin, and depending on the result of the decision, RL is increased or decreased. These steps are repeated, with the amount of the increase or decrease being reduced, e.g., halved each time.

It is also possible to first set the resistance RL at the maximum value RLmax, and after confirming that Vp is smaller than Vmin, to then reduce the load resistance RL to about ½ of a maximum value RLmax. After that, the load resistance which makes $$Vmax > Vp > Vmin$$

is sought in a manner similar to that described above.

Figure 8:
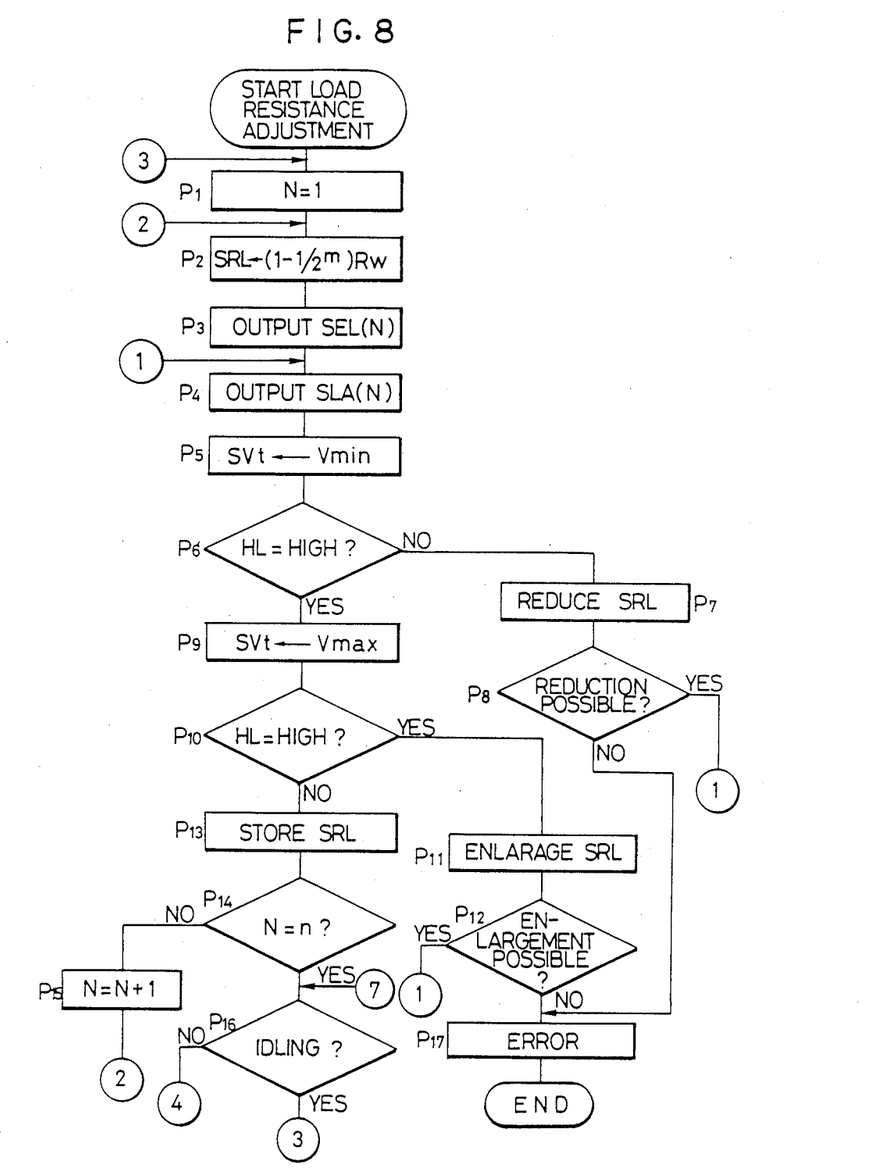
FIG. 8 is a flowchart illustrating an example of operation during adjustment of the load resistance.

FIG. 8 illustrates an example of the above procedure. FIG. 8 will now be used to gain a better understanding.

First, to conduct the adjustment for the sensor S1, the sensor number N is set at 1 at the step P1.

Then, the control unit 16 sets U1 to Um at "1" and supplies load resistance designating data consisting of U1 to Um as the load resistance selecting data SU to the load resistance unit 6. As a result all the switches SW1 to SWm are opened to set the load resistance RL at the maximum value $RLmax = (1 - \frac{1}{2}^m) Rw$ (P2).

The control unit 16 then supplies the sensor selecting data SEL to the sensor selector 4 and the latch element selecting data SLA to the latch controller 12 (P3, P4). The control unit 16 also supplies the lower limit setting data SVmin, designating the lower limit voltage Vmin for the particular sensor, to the comparator unit 7 (P5).

The comparator unit 7 compares the sense output voltage Vp with the threshold voltage Vt, which is now Vmin designated by SVmin. The output of comparator unit 7 is the binary signal HL, which is either High or Low depending on the result of the comparison. The comparator output signal HL is latched by the latch element (in this case, FF1) corresponding to the sensor S1, and is thereafter read by the control unit 16.

The control unit 16 reads the latched signal HL to see whether it is High or Low (P6). If it is Low, it means that the sense output voltage Vp is smaller than Vmin, so the load resistance RL is decreased in order to increase the gradient of the line L1 (P7). In this case, U1 is changed to "0" to approximately halve the load resistance RL, or more precisely reduce it to:

$$(1-\tfrac{1}{2}-\tfrac{1}{2}^m)Rw.$$

A decision is made whether the reduction was possible (P8), and if it was possible, the steps P4, P5 and P6 are repeated.

As an alternative, it is possible to transit from the step P8 to the step P6, omitting the steps P4 and P5.

If, as a result of the decision at the step P6, the latched comparator output signal HL is Low, it means that the sense output voltage Vp is smaller than Vmin, so the load resistance RL is further reduced to further increase the gradient of the line L1 (P7). If the reduction was possible (P8), the steps P4 to P8 are repeated with the reduced load resistance.

If the comparator output signal HL is found to be High at step P6, the control unit 16 supplies the comparator unit 7 with an upper limit setting data SVmax, designating the upper limit voltage Vmax for the particular sensor (P9). A decision about the level of the comparator output signal HL, similar to that of the step P6, is then conducted (P10).

If the comparator output signal HL is found to be High at step P10, the sense output voltage Vp is larger than Vmax, so the load resistance is enlarged (that is, increased) to decrease the gradient of the line L1 (P11). A decision is made as to whether the enlargement was possible (P12), and if it was possible, steps P4 to P8 or steps P4 to P12 are repeated. If, as a result thereof, the comparator output signal HL becomes Low (P10), the value of the load resistance RL, i.e., the values of SU (U1 to Um), are stored as the load resistance setting data SRL in the memory unit 13 (P13).

In this way the load resistance RL is adjusted, by reduction (P7) or enlargement (P11), and when it is confirmed that the sense output voltage Vp is larger than Vmin (P6) and smaller than Vmax (P10), the load resistance RL is considered to be the optimum value. The corresponding data SU is stored in the memory unit 13 as the load resistance setting data SRL for the sensor.

The above operation is repeated for all the sensors. That is, until the sensor number N becomes n (P14), N is incremented by 1 (P15), and procedures similar to these described above are repeated for the sensor identified by the new value of N. When N reaches n (P14), a decision is made as to whether the medium handling apparatus 19 is still idling, i.e., whether the load resistance adjustment may be continued (P16). If that is permitted, the processing described above is repeaded, by returning to the step P1.

If at step P8 it is found that the reduction at the preceeding step P7 was impossible, that is, when the values of U1 to Um were all "0" before the reduction, or if a step P12 it is found that the enlargement at the preceding step P10 was impossible, that is, when the values of U1 to Um were all "1" before the enlargement, an error is detected and displayed (P17) and the operation is stopped.

Operation of the medium detecting system in the medium detecting mode will now be described.

When a signal for starting operation in the medium detecting mode is supplied from the interface in the medium handling apparatus 19 to the control unit 16, the control unit 16 then instructs the data switching unit 14, the address switching unit 15, and the control signal switching unit 20 to operate in the medium detecting mode, by means of the switch control signals 14s, 15s and 20s. The control unit 16 also instructs the synchronous signal generator 17 to operate.

Then, the data switching unit 14 separates the data bus for the control unit 16 from the data bus for the memory unit 13, the address switching unit 15 connects the address bus for the address generator 18 with the address bus for the memory unit 13, and the control signal switching unit 20 opens the signal paths from the control unit 16 to the memory unit 13, and supplies memory control signals which inhibit rewriting of the data in the memory unit 13.

The address generator 18, being supplied with the clock signals CLK from the synchronous signal generator 17, generates addresses for the memory sections 13a to 13d. As was previously noted these memory selections store the sensor selecting data SEL, the load resistance setting data SRL, the reference setting data SVr and the latched comparator output signals HL. The addresses are generated in order from the sensor S1 to the sensor Sn, and from the memory sections 13a to 13d. When the address generator 18 generates all the addresses in the memory sections 13a to 13d, up to the last address (the address for the signal HL (n) for the last sensor Sn in the memory section 13d), it then generates the first address (the address for data SEL(1) for the sensor S1 in the memory setion 13a). In this way, it accesses the memory locations in the memory sections 13a to 13d cyclically.

Figure 9:
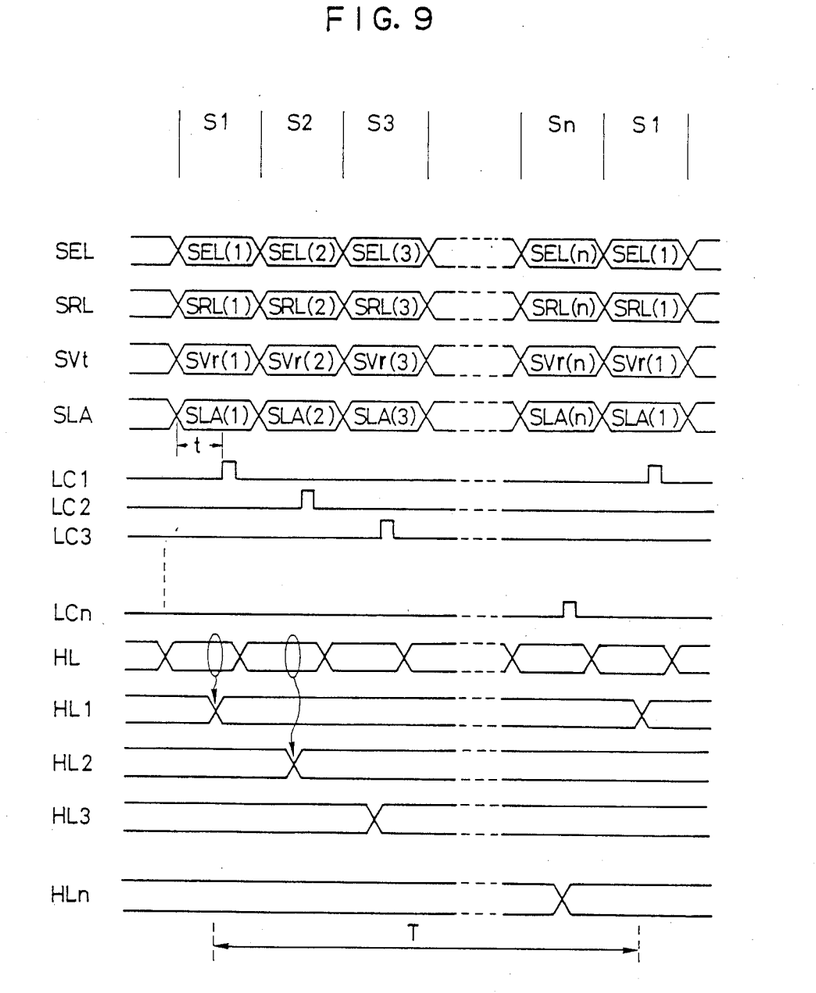
FIG. 9 is a time chart illustrating operation during detection of the medium.

The memory unit 13 produces the sensor selecting data SEL, the load resistance setting data SRL, the reference setting data SVr and the latch element selecting data SLA tht are stored at the memory locations designated by the addresses from the address generator 18. The production of the data are made at the timings shown in FIG. 9.

The load resistance unit 6 sets the load resistance RL on the basis of the load resistance setting data SRL. Also, the sensor selector 4 connects the collector of the photo-trnsisitor 3 of the selected sensor to the node Q, while connecting the collectors of the photo-transistors 3 of the nonselected sensors to the ground.

The photo-curent Ic flowing through the photo-transistor 3 of the selected sensor is converted into a voltage sisgnal, which is the sense output voltage Vp, by the load resistance unit 6 connected via the impedance converter 5.

The comparator unit 7 compares the sense output voltage Vp with the threshold voltage Vt, which is now the reference voltage Vr set by the reference setting data Svr, and generates the vinary signal HL.

Upon expiration of the time required for the comparator output HL to stabilized, and responsive to the synchronous signal CLK supplied from the synchronous signal generator 17 to the latch controller 12, a latch clock signal is supplied to the latch element (one of FF1 to FFn) selected by the latch element selecting data SLA.

The control unit 16 periodically reads the latched comparator outputs HL1 to HLn and determines whether these signals ar High or Low. In doing so, it may adopt a procedure by which it recognizes a true "High" if the latched comparator outputs are found to be High consecutively for a predetermined number of times (e.g., three times), to eliminate the effects of noises. The results of the High/Low determination are sent to the medium handling apparatus 19.

When a signal for terminating operation in the medium detecting mode is supplied from the interface in the medium handling apparatus 19 to the control unit 16, the control unit 16 instructs the data switching unit 14, the address switcing unit 15 and the control signal switching unit 20 to stop operating in the medium detecting mode, and to enter the load resistance adjusting mode, by means of the switch control signals 14s, 15s and 20s. The control unit 16 also instructs the clock signal generator 17 to stop operating in the medium detecting mode. Operation in th medium detecting mode is thereby terminated, and operation is the load resistance adjusting mode is started.

Now the advantage of using the sensor selector 4, which connects the collectors of the photo-transistors 3 of the nonselected sensors to the ground, will be described.

When there is a transistion from a state in which one of the sensors, e.g., the sensor S1, is selected (as depicted in FIG. 2) to a stat in which another sensor, e.g., the sinsor S2, is selected, it takes a certain time before the output of the sensor at the sense output node P, and hence the comparator output, are stablized. The length of time required for this stabilization is shortened in the invention. This will be explained next.

Figure 10:
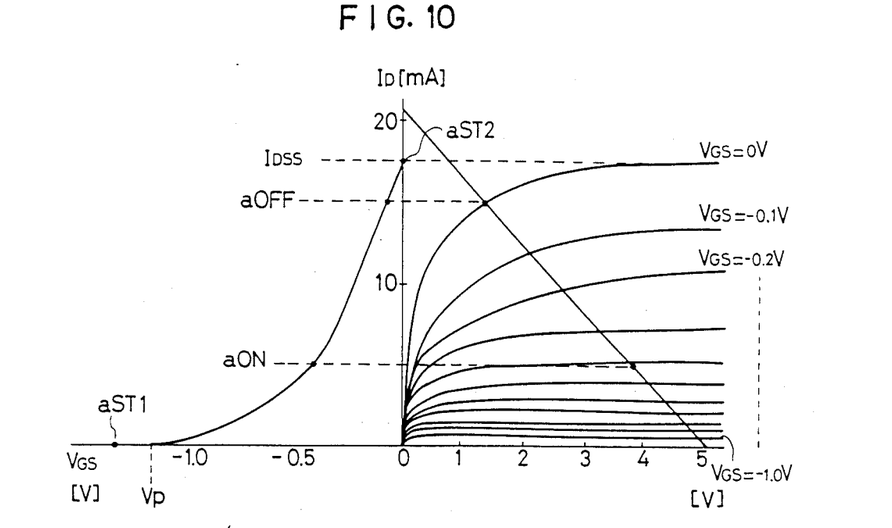
FIG. 10 is a diagram illustrating an example of the characteristics of the FET used as the impedance converter 5 in FIG. 1.
Figure 11:
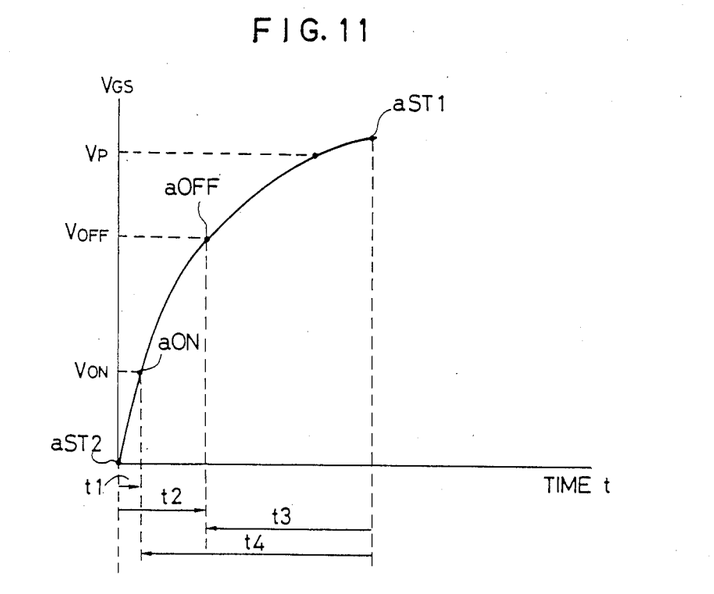
FIG. 11 is a diagram illustrating an example of the characteristics of the photo-transistor 3 in FIG. 1.

The characteristic of the FET used as the impedance converter 5 are shown in FIG. 10, while the characteristics of the photo-transistor 3 are shown in FIG. 11. In these figures, $I_D$ represents the current flowing from the power supply Vcc through the load resistance circuit 6 into the the drain of the FET, $V_{DS}$ represents the drain-source voltage of the FET, and $V_{GS}$ represents the gate-source voltage of FET. $I_{DSS}$ represents the drain current at the time of zero-bias, $V_{PO}$ represent the gate-source cut-off voltage (pinch-off voltage), and aON and aOFF respectively represent the operating points in the medium-present and medium-absent consitions.

In the state shown in FIG. 2, the photo-transistor 3 of the sensor S2 is not selected and its collector is grounded, so it is at the ground potential (zero potential). The operating points on FIG. 10 and FIG. 11 are at aST2.

This is in contrast to the case in which the collectors of the photo-transistors 3 of the nonselected sensors are not grounded and are floating. In this case, the operating points would be at aST1 in FIG. 10 and FIG. 11.

When the sensor S2 is selected, and collector of the photo-transistor 3 of the sensor S2 is connected to the node Q, the collector pontential Vx will becomoe equal to $V_{GS}$, which is the gate-source voltage of the FET 5a. If the medium is present, the operating point moves to aON. If the medium is not present, the operating point moves to aOFF.

The time required for the movement of the operating point from aST2 to aON is indicated by t1 and the time required for the movement from aST2 to aOFF is indicated by t2, as shown in FIG. 11. This should be compared with the times t4 and t3, respectively, which are required for the operating point to move from aST1 to aON and aOFF. It will be seen that t1 and t2 are shorter thtn t4 and t3, respectively. This, means the time to (FIG. 9) which must be allowed for the comparator output HL to stabilize can be shortened. This also contributes to an increase in the speed of operation during the medium detecting node.

As has been described, according to the invention, the load resistance is automatically set and updated for optimization for each of the sensors, and the medium detection is performed using the updated, optimum load resistance. As a result, it is possible to cope with variations in the characteristics of the light-emitting elements and the light-receiving elements, variations from the true alignment between the light-emitting elements and the light-receiving elements, and variations in the percentage of light which is transmitted from a light-emitting element to its light-receiving element, due for example to the amount of dust on the light-receiving element.

Where the data switching unit 14, the address switching unit 15 and the control signal switching unit 20 are used and data is transferred from the memory unit 13 to the sensor selector 4, the load resistance unit 4, etc., without intervention of the control unit 16 during the medium detecting mode, the speed of operation is increased. Detection of the medium can therefore be accomplished at a high speed, and at a high resolution. It is therefore possible to detect smaller broken regions of the medium, inclined travel (skew) of the medium, and small spacing between the adjacent media, and to measure the length of the medium.

Use of the sensor selector 4, which grounds the collectors of the photo-transistors 3 of the nonselected sensors, provides the advantage of a further increase in the operating speed.

What is claimed is:

1. A medium detecting system, comprising:
    a plurality of optical sensors, each including a light-emitting element and a light-receiving element disposed to confront each other so that a medium interposed between the light-emitting element and the light-receiving element interrupts the light transmitted from the light-emitting element to the light-receiving element, the electric current flowing through the light-receiving element varying with the amount of light received by it;
    a load resistance unit means, provided in common for the plurality of sensors, for varying the load resistance responsive to load resistance selecting data;
    a sensor selector means, responsive to sensor selecting data, for selecting one of the sensors and connecting the light-receiving element of the selected sensor to the load resistance unit means; and
    a rewritable memory unit means for storing the sensor selecting data and load resistance setting data for the respective sensors, said load resistance setting data being supplied as said load resistance selecing data to the load resistance unit means.

2. A system according to claim 1, wherein the light-receiving element of the selected sensor and the load resistance unit are connected in series with each other via a sense output node, and said system further comprises a comparator unit means for comparing the voltage at the sense output node with a threshold voltage, to produce a binary signal whose values indicates the result of the comparison.

3. A system according to claim 2, wherein said comparator unit, means comprises a digital-to-analog converter receiving threshold selecing data and producing an analog threshold voltage, and voltage comparator element receiving the voltage from said sense output node and the threshold voltage from the digital-to-analog converter.

4. A system according to claim 3, further comprising a control unit means for adjusting the load resistance to be the optimum value for each sensor, such that when no medium is present at a particular sensor the voltage at said sense output node is larger than a predetermined lower limit voltage and is smaller than a predetermined upper limit voltage.

5. A system according to claim 4, wherein said control unit means comprises means for applying lower limit data designating the lower limit voltage and upper limit data designating the upper limit voltage to the digital-to-analog converter during the adjustment of the load resistance.

6. A system according to claim 4, wherein said control unit means comprises means for writing data indicating the optimum load resistance, as said load resistance setting data, into the memory unit means.

7. A system according to claim 6, wherein the system is operable in a load resistance adjusting mode and in a medium detecting mode, and wherein in the load resistance adjusting mode:
the sensor selecting data is read from the memory unit means and supplied to the sensor selector means,
load resistance designating data is generated by the control unit means and supplied as the load resistance selecting data to the load resistance unit means,
the load resistance designating data is successively changed until the optimum value of the load resistance, making the sense output voltage larger than a predetermined lower limit voltage and smaller than a predetermind upper limit voltage, is found, and
the load resistance designating data satisfying above condition is stored as the load resistance setting data in the memory unit means.

8. A system according to claim 7, wherein the successive change of the load resistance designting data is conducted in a manner in which the sense output voltage is compared with the upper and lower limit voltages to determine whether the load resistance should be increased or decreased in order for the sense output voltage to be larger than said lower limit voltage and smaller than said upper limit voltage.

9. A system acording to claim 8, wherein the successive change is carried out by binary search.

10. A system according to claim 6, wherein the system is operable in a load resistance adjusting mode in a medium detecting mode, and wherein, in the medium detecting mode:
the sensor selecting data is read from the memory unit means and supplied to the sensor selector means,
the load resistance setting data for the sensor designated by the sensor selecting data is read from the memory unit and supplied as the load resistance selecting data to the load resistance unit means, and
the sense output voltage derived then is compared with the threshold voltage which is then the reference voltage for the selected sensor ro determine the presence or absence of the medium at the selected sensor.

11. A system according to claim 10, wherein the reference voltage is designated by reference setting data for the sensor, the reference setting data being dtored in the memory unit means.

12. A system according to claim 6, wherein the system is operable in a load resistance adjusting mode and in a medium detecting mode, wherein said control unit mean comprises means for generating addresses for reading the sensor selecting data from the memory unit means in the load resistance adjusting mode, and wherein said system further comprises:
an address generator means for generating addresses for reading the sensor selecting data and the load resistance setting data from the memory unit means in the medium detecting mode, and
a switching unit means for permitting application of addresses from the control unit means to the memory unit means and application of the sensor selecting data from the memory unit means to the control unit means in the load resistance adjusting mode, and for permitting application of the addreses from the address generator means to the memory unit means, and application of the sensor selecting data and load resistance setting data from the memory unit means to the sensor selector means and the load resistance unit means directly, so as to bypass the control unit means, in the medium detecting mode.

13. A system according to claim 2,
wherein each of said light receiving elements is a photo-transistor having an emitter and a collector,
wherein the emitters of the photo-transistors of all the sensor are connected to a node at a first potential, and
wherein said sensor selector means comprises means for connecting the collector of the photo-transistor of the selected sensor to the load resistance unit means, and for connecting the collectors of the photo-transistors of the nonselected sensors to said node at said first potential.

* * * * *